United States Patent [19]

Foody et al.

[11] Patent Number: 5,755,928
[45] Date of Patent: May 26, 1998

[54] METHOD FOR AUTOMATED MONITORING OF PULP RETENTION TIME USING AN IODIDE SALT AS A TRACER

[75] Inventors: Patrick J. Foody, Ottawa; Brian W. Creber, Dun Robin, both of Canada

[73] Assignee: Iogen Corporation, Ottawa, Canada

[21] Appl. No.: 568,516

[22] Filed: Dec. 7, 1995

[51] Int. Cl.$^6$ .................................................. D21C 7/12
[52] U.S. Cl. ........................... 162/49; 162/61; 162/238
[58] Field of Search ........................... 162/49, 238, 65, 162/251, 252, 259, 62, 61, 72, 87, 88, 89, 198

[56] References Cited

U.S. PATENT DOCUMENTS

| | | | |
|---|---|---|---|
| 4,295,927 | 10/1981 | Bentvelzen et al. | 162/57 |
| 4,298,426 | 11/1981 | Torregrossa et al. | 162/57 |
| 4,298,427 | 11/1981 | Bentvelzen et al. | 162/57 |
| 4,783,314 | 11/1988 | Hoots et al. | 422/3 |
| 4,946,555 | 8/1990 | Lee et al. | 162/49 |
| 5,034,095 | 7/1991 | Kido et al. | 162/65 |

OTHER PUBLICATIONS

Vernon B. Bodenheimer, "Channeling in Bleach Towers and Friction Losses in Pulp Stock Lines", Southern Pulp and Paper Manufacturer, pp. 42–44, & 46 (1969).

J.K. Perkins, Channeling in Continuous Bleaching Cells* (Pulp Behavior Patterns in Bleach Towers), A talk given at Gulf Coast Section TAPPI, pp. 191–198 (1971).

Carlton W. Dence, et al., "Chlorination—The Bleaching of Pulp", Third Edition, Revised, TAPPI Press, pp. 29 & 62.

George Tchobanaglous, et al., "Wastewater Engineering—Treatment Disposal & Reuse", McGraw-Hill, Inc., Third Edition, pp. 1214–1216 (1991).

Manual for Orion Electrode, Orion Research Incorporated Laboratory Products Group, pp. 2–29 (1991).

*Primary Examiner*—Steven Alvo
*Attorney, Agent, or Firm*—Fitzpatrick, Cella, Harper & Scinto

[57] ABSTRACT

An automated system and method for measuring the residence time of wood pulp as it moves through various stages of processing in a pulp mill. A tracer compound comprising a neutral salt of a halogen is introduced into a first location in the path of the pulp slurry; at a second location an automated detector detects the concentration of tracer compound over a time period; a controller relays a voltage signal from the detector to a processor which uses a calibration curve to integrate tracer concentration over time and thereby derive pulp residence, between the first and second locations.

10 Claims, 2 Drawing Sheets

METHOD FOR AUTOMATED MONITORING OF PULP RETENTION TIME USING AN IODIDE SALT AS A TRACER

BACKGROUND OF THE INVENTION

1. Field of the Invention

The present invention relates to an automated tracer system for measuring the residence time of wood pulp as it moves through various stages of processing in a pulp mill. The invention comprises a tracer compound for introduction into a pulp slurry, an automated detector for detecting the presence of the tracer compound in the pulp slurry, a controller for relaying a voltage signal from the detector to a processor, and a processor for converting the voltage signal to a calibration curve to determine the amount of tracer detected in the pulp slurry. The present invention also relates to methods for measuring the residence time of pulp in a pulp slurry using the foregoing automated tracer system. The present invention will enable pulp mill personnel to determine conveniently, economically and more accurately than has heretofore been possible, the residence time distribution of pulp as it moves through the various pulp processing steps at a pulp mill. This, in turn, will enable pulp mill personnel to better control the operating conditions under which the pulp is processed and thereby ensure a higher quality final product.

2. Brief Description of the Prior Art

The modern production of most paper pulp is primarily based on two chemical processes: pulping and bleaching.

Pulping involves a combination of chemical impregnation, heat and force to break apart wood fibers into pulp. The pulping operation uses mechanical debarking and grinding of wood chips, followed by cooking in chemical liquor. In chemical pulping, the cooking is carried out in a large tower called a digester. The chemical liquor can be alkali (as in the Kraft process), acidic (as in the sulfite process) or neutral (as in the chemi-thermo-mechanical process).

Bleaching uses oxidizing chemicals to remove some or all of the lignin from the pulp, increasing its brightness and strength and improving such properties as absorption of printing ink, opacity, etc. Bleaching takes place in stages entailing the sequential use of from 1 to about 7 different chemicals, depending on the desired properties of the final pulps. The various bleaching stages are well known to those skilled in the pulp bleaching art and are sometimes referred to by reference to the chemical reactors used to carry out the reactions of chemicals with pulp. Commonly used chemicals in bleaching stages are oxygen, chlorine, chlorine dioxide, sodium hydroxide, hydrogen peroxide, sodium hydrosulfite, and xylanase enzymes.

Like all chemical processes, pulping and bleaching have key variables that must be controlled to obtain efficient use of chemicals and an acceptable final product. The key variables in pulping and bleaching are temperature, pH, chemical concentration, and reaction time.

The method used in most pulping and bleaching processes to carry out the reactions involves pumping the pulp continuously through towers. Typically, the pulp slurries are comprised of 1.5% to 30% pulp solids in aqueous liquor and are pumped through pipes and into or out of the towers. The processes are carried out by adding chemicals to the pulp slurry at or within the entrance to the towers. The pulp then flows through the towers, either upward or downward depending on the process and the mill. The towers hold the pulp within a closed environment, which is beneficial for controlling pH, temperature, and especially chemical concentration. For example, in the case of enzyme treatment of Kraft pulp to enhance bleaching, the process is usually carried out by flowing the pulp down a tower as a slurry of about 8% solids in water at 50° C., and a pH of 7.5. This is accomplished in an enzyme tower that might require about one hour for the pulp to traverse, given the pulp production rate in the mill. For a modern mill that produces 1000 tonnes of pulp per day, this might be a tower 30 meters tall and 8 meters in diameter that is about ½ full.

In contrast to pulp pH, temperature, and chemical concentration, which are carefully monitored and controlled by on-line instrumentation, pulp retention time is not measured routinely. The reasons for this neglect relate to the expense, inconvenience and inaccuracy presently encountered by pulp mill operators when employing the prior art detection methods that are now commercially available. Because of these problems, pulp retention time is frequently inferred (i.e., calculated) rather than measured based on the amount of pulp in the tower, the pulp throughput, and by assuming that the pulp flows as a uniform plug through the tower; using a technique known as "plug flow". In the above example, the tower contains 50.2 tonnes of pulp (at 8% solids consistency); at a production rate of 1000 tonnes per day, the retention time for ideal plug flow is 1.2 hours.

A "plug flow retention time" is often quoted because it is readily calculated. However, that time value is often inaccurate because pulp does not generally travel through a tower uniformly as a plug. Rather, the pulp moves more quickly as a core through the center of the tower, by a phenomenon known as "channeling". Pulp channeling was described in detail by Bodenheimer, *Channeling in Bleach Towers and Friction Losses in Pulp Stock Lines*, Southern Pulp and Paper Manufacturer, Sept. 1969, pp. 42–46 (hereafter "Bodenheimer"). In the example of pulp treated with enzymes, a loss of actual retention time due to channeling causes undertreating of the pulp, which in turn causes inferior bleaching of the pulp thereafter.

Channeling is difficult to observe directly because the inside of the tower is not usually open to view. Bodenheimer reported that the tendency for pulp to channel and the speed with which the pulp traverses the tower is influenced by the tower geometry, pulp level in the tower, wood species, solids consistency, temperature, and pH of the pulp. Of these, only the pulp level can be changed arbitrarily day-to-day, so many mills characterize the retention time at a given tower pulp level and try to maintain that level.

It is known to use tracer systems in the pulp processing art to measure true retention time in a tower. It also is known to use a chemical compound as a tracer to measure retention time by adding it to a pulp slurry of at least about 1.5% solids consistency at the entrance of the tower as a sudden "spike" and to monitor the breakthrough of tracer at the tower outlet. At or above about 1.5% solids consistency, the tracer travels with the pulp and does not migrate significantly into the free liquid continuous phase. Lithium Chloride is the most commonly-used tracer system in the pulp industry. Perkins, *Channeling in Continuous Bleaching Cells (Pulp Behavior Patterns in Bleach Towers)*, Jan. 1971, pp. 191–98 (hereafter "Perkins") describes the use of lithium chloride as a tracer compound, which is measured by an atomic absorption analysis on the pulp slurry. The use of lithium chloride as a tracer compound, although it is the standard method in the industry, suffers from some significant disadvantages—it is expensive to use (costing approximately $5,000 per tracer test) and the analysis is time consuming. Dence and Annergren, in Chapter 3 "Chlorination", p. 62 in *The Bleaching of Pulp*, R. Singh, Ed., Tappi Press, 1979 also suggest use of trace metals, such as lithium, as a tracer compound, which also are to be detected by employing atomic absorption techniques.

Metcalfe and Eddy, *Wastewater Engineering*, McGraw-Hill, 1991, p. 1214–1216 recommend sodium chloride and dyes as tracer compounds for a range of systems other than pulp. Unfortunately, sodium chloride has the disadvantage that it is already present in pulp slurry in concentrations of about 50 ppm, not counting that already associated with the chlorine in the bleach, which is of a much higher concentration. Because of this fact, the quantity of sodium chloride required for use in a tracer test is inconveniently large and difficult to handle at the paper mill. Such dyes also discolor the pulp, which is unacceptable to the pulp customer, and can be destroyed by residual levels of bleaching chemicals present in a pulp mill.

Lee et al. (U.S. Pat. No. 4,946,555) ("Lee et al.") describe the use of an inert tracer gas (helium) in a pulp and paper mill in order to determine the utilization of oxygen by an aqueous cellulosic pulp. Although helium may be useful in monitoring the flow of gaseous chemicals inside of a tower, helium gas does not become impregnated into the pulp and thus cannot be used to derive the retention time of the pulp. In addition, helium tracer is not at all useful in downflow towers because of its buoyancy.

Most tracer tests today are carried out with manual sampling at the tower exit and off-line analysis of the tracer. In manual sampling, samples are typically collected periodically (often as frequently as every five minutes) at the tower exit after the introduction of tracer compound into the tower. This method allows pulp mill operators to determine the length of time required for the breakthrough of tracer at the tower exit. However, because the samples are taken at discrete intervals, there is the real possibility that some tracer breakthroughs may not be detected. Moreover, because of the effort and expense involved, tracer tests using manual sampling are typically not carried out more than once every 6 months.

An alternative to manual sampling is on-line analysis of the tracer concentration. While on-line analysis overcomes some the drawbacks in manual sampling, the limited experience in pulp mills using on-line tracer testing has not been successful. Perkins described the use of radioactive tracers and detection by a Geiger counter. This method is now generally considered unsuitable because radioactive tracers are potentially hazardous and their use is frequently restricted by government regulations.

SUMMARY OF THE INVENTION

The present invention overcomes the above deficiencies associated with the use of conventional tracer-detecting systems by enabling pulp mill operators to determine conveniently, economically and more accurately than has heretofore been possible, a residence time distribution of pulp as it moves through the various pulp processing steps at a pulp mill. This, in turn, will help ensure a higher quality end product by providing a means to better control the operating conditions under which the pulp is processed at pulp mills.

The inventors have developed an accurate, convenient, and inexpensive system for measuring the residence time of wood pulp as it moves through a pulp mill. The invention relates to an automated tracer system comprising a tracer compound for introduction into a pulp slurry, an automated tracer detector for detecting the presence of the tracer compound in the pulp slurry, a controller for relaying a voltage signal from the detector to a processor, and a processor for converting the voltage signal to a calibration curve to determine the amount of tracer detected in the pulp slurry. The present invention offers several unexpected advantages over conventional methods for determining the residence time of wood pulp in a pulp mill. For example, the inventors have found that the present invention permits pulp mill operators to conduct tracer tests much more accurately, conveniently and inexpensively than has been possible using conventional pulp mill detecting systems, including other on-line detecting systems. The present invention also allows a single operator, with limited training, to conduct several tracer tests per day.

Using the present invention the inventors have found, quite unexpectedly and contrary to conventional pulp mill practice, that not only does pulp frequently not traverse a tower in a "plug flow" mode with a uniform retention time, but rather closely adjacent control volumes of pulp often will move between a first and a second location at widely differing retention times. Through use of the present invention, applicants have also been able to offer an explanation for the nonuniform bleaching sometimes observed in pulp following a chemical treatment step.

Using the present invention the inventors also have found, quite unexpectedly and contrary to conventional pulp mill practice, that the retention time in a given tower can vary by as much as 2-fold even when the tower level, pulp species, pH, temperature, and solids consistency are held constant. This is directly contrary to the findings of Bodenheimer, who reported that such a set of variables are determinative of pulp retention time in a tower.

Through the use of their invention, the inventors have provided a means for pulp mill operators to measure pulp residence time on an on-line basis, thereby permitting the operator to adjust the operating conditions of the pulp slurry based on actual, rather than assumed, retention times. Tracer systems heretofore known in the pulp processing art have proved inadequate to achieve such a goal for a variety of reasons, including prohibitive expense, long sampling time requirements, inconvenience to run, safety concerns, and poor data resolution.

BRIEF DESCRIPTION OF THE DRAWINGS

The invention is illustrated in a preferred embodiment by reference to the accompanying drawings in which.

DETAILED DESCRIPTION OF EMBODIMENTS

The present invention relates to an automated tracer system comprising a tracer compound for introducing an iodine salt tracer into a pulp slurry at a first location; an automated tracer detector for detecting over a time period the concentration of tracer compound in the pulp slurry at a second location; a controller for relaying a voltage signal from the detector to a processor, and a processor for calibrating the voltage signals to tracer concentration via a calibration curve, so that the time function of tracer concentration will indicate the residence time of pulp slurry passing by the second location. The present invention thereby enables pulp mill operators to measure accurately the residence time distribution of pulp at various stages of processing in a pulp mill. The present invention also encompasses methods of determining the residence time of pulp in a pulp mill using the foregoing automated detection system.

In a preferred embodiment, which is described with reference to FIG. 1, the present invention relates to an automated detection system wherein the tracer compound is a halogen salt. In or more preferred, embodiments the tracer compound is an iodide salt, wherein the automated tracer detector is an iodide detecting electrode, and wherein the tracer solution is introduced into the pulp slurry at the entrance of an enzyme treatment tower and detected at the exit of that tower.

In this embodiment, the iodide salt may be any neutral salt of iodine, although sodium iodide, potassium iodide, and mixtures thereof are preferred. To determine the residence time distribution of pulp in a pulp slurry of a conventional 1000 tonne per day stock line about 0.1 to 5 Kg of iodide salt is required, and more preferably about 0.5 Kg of iodide salt.

Figure 1:
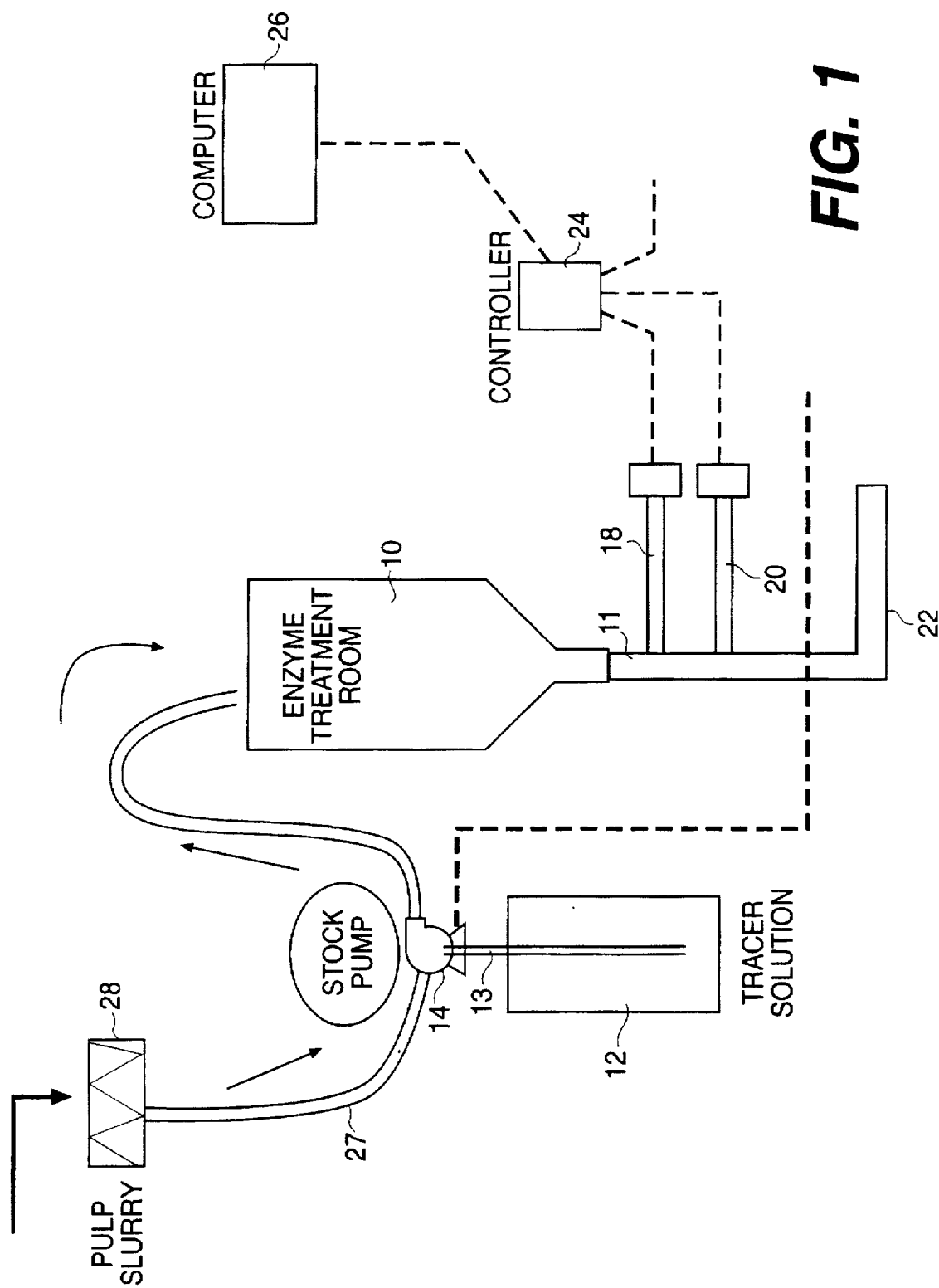
FIG. 1 is a schematic representation of a tracer system of the present invention for measuring the residence time of pulp slurry in an enzyme treatment tower of a pulp and paper mill.

Prior to the introduction of the iodide salt into the pulp slurry, the iodide salt is preferably first dissolved in water to form an iodide salt solution depicted as tracer solution 12 in FIG. 1. To maintain reasonable volumes, concentrations of from 15% to 25% by weight of iodide salt are preferred. The iodide solution can be stabilized against long-term decomposition into iodine gas by adding 0.1 to 25 grams of sodium hydroxide per liter, preferably about 1 gram per liter. Typically, a 40 gallon barrel holds enough iodide solution for about 50 tracer tests to be conducted.

The tracer solution may be added to the pulp slurry at various stages of the pulping process. In this embodiment, the tracer solution is added to the suction inlet of stock pump 14 through chute 13. The pump, which can be a conventional stock pump or a medium consistency (MC) pump, mixes the tracer solution into the pulp slurry and conveys the slurry to the entrance of enzyme treatment tower 10, also called the brownstock storage tower. The tracer may alternatively be added to the pulp before the pulp reaches the stock pump, such as at the repulper 28 or into chute 27 leading to the stock pump. The tracer solution may be added to the pulp slurry, manually or by means of a pump. When added manually, the tracer solution is preferably poured onto the pulp quickly to approximate a "spike" addition. When added by pump, the tracer solution is added as desired by automated means. Automated addition offers the added advantages of remote addition of the tracer and convenience when an operator is running many tracer tests.

At exit 11 of enzyme treatment tower 10, the pulp slurry is diluted to about 3.0% solids, by weight, consistency with a chlorine bleach effluent. The slurry then passes through a mixing pump (not shown in FIG. 1) and pipe 22 on its way to the chlorination tower.

The iodide detecting electrode of the present invention comprises one or more electrodes whose sensitivity to iodide is unaffected by the presence of chloride, sulfate, or other compounds frequently found in pulp slurry. If two electrodes are used as depicted in FIG. 1, a first electrode 18 is used to detect the iodide in the pulp slurry and a second electrode 20 is used as a reference electrode. Alternatively, a single combination electrode (not shown in FIG. 1) can be used to accomplish the same purpose. An example of an iodide-sensitive electrode suitable for use in the present invention is the Orion 94-53 Halide Electrode which is available commercially from Orion Research Inc., Boston, Mass. The inventors have found it desirable to modify the Orion electrode by substantially encasing it in a 1 inch diameter titanium sleeve to protect it against corrosion from compounds found in the pulp slurry. A grounded Ag/AgCl reference electrode with temperature compensation is found on a standard pH meter. These electrodes are mounted in the stock line approximately 12 inches apart through a 1.25 inch hole. In the preferred embodiment, iodide sensitive electrode 18 and reference electrode 20 are mounted on pipe 22 leading to a chlorination tower.

A controller is used to process signals generated by the detecting electrodes. In this embodiment, controller 24 is used to process signals generated by electrodes 18 and 20 and to convert them into an iodide concentration reading.

Any programmable logic controller for relaying voltage signals may be used as the controller in practicing the present invention. An example of such a controller is the model 352 controller made by Moore Products Co., of Spring House, Pa. which is currently in use in many pulp mills. The controller relays the voltage signal from the iodide detecting electrode to a processor depicted as computer 26 in FIG. 1, where it is converted to a concentration reading based on the calibration curve for the electrode.

Any industrial computer for conducting mathematical calculations based on voltage input may be used in practicing the present invention. An example of such a computer is the Texas Micro Model D486DX33 computer made by Texas Instruments which is presently in widespread use. The calibration curve is developed based on the voltage response of several iodide solutions of known concentration. Any industrial data-acquisition software may be used to calculate the calibration curve and use it to convert the voltage signal to an iodide concentration. An example of such software is the GE Fanuc Series 90-30 Programming software, available from General Electric Company. The software also retrieves the time elapsed since the introduction of tracer from the internal clock in the computer. The software determines the amount of tracer recovered by integrating the tracer concentration over time. The software then determines the average residence time by carrying out the integration of the time-weighted concentration (C times t) over time and dividing by the total amount of tracer recovered.

The detector registers the iodide concentration continuously after the addition of tracer. The duration of tracer monitoring is set by the user and can be for a specified period of time or until a specified amount of tracer is recovered or based on some other criteria.

In a second embodiment, the present invention is as described above in connection with the preferred embodiment except that: (1) the tracer solution is introduced into the pulp cooking liquor slurry at the entrance of a digester and detected after the exit of the digester, when cooled to about 70° C.–80° C., (2) the slurry is about 30% solids consistency, and (3) the iodide electrodes are mounted after the exit of a blow tank or cooking zone so that the maximum operating temperature of the particular electrode will not be exceeded.

In a third embodiment, the present invention is as described above in connection with the preferred embodiment except that: (1) the tracer solution is introduced into the pulp slurry at the entrance of an oxygen delignification reactor and detected at the exit of the reactor, (2) the slurry is 5% to 15% solids consistency, and (3) the iodide electrodes are mounted at the exit of the cooking stone.

In a fourth embodiment, the present invention is as described above in connection with the preferred embodi-

7 ment except that: (1) the tracer solution is introduced into the pulp slurry at the entrance of an ozone reactor and detected at the exit of the reactor, (2) the slurry is 3% to 15% solids consistency, and (3) the iodide electrodes are mounted at the exit of the reactor.

In a fifth embodiment, the present invention is as described above in connection with the preferred embodiment except that: (1) the tracer solution is introduced into the pulp slurry at the entrance of a chlorine reactor and detected at the exit of the reactor, (2) the slurry is 1.50% to 10% solids consistency, and (3) the iodide electrodes are mounted near the stock pump at the exit of the reactor or at the washer vat after the reactor. One skilled in the art will appreciate that the chlorine reactor may contain chlorine, chlorine dioxide, or mixtures thereof. In a sixth embodiment, the present invention is as described above in connection with the preferred embodiment except that: (1) the tracer solution is introduced into the pulp slurry at the entrance of an alkali extraction reactor and detected at the exit of the reactor, (2) the slurry is 4% to 14% solids consistency, and (3) the iodide electrodes are mounted near the stock pump at the exit of the reactor or at the washer vat after the reactor. One skilled in the art will appreciate that the alkali extraction reactor may contain sodium hydroxide, hydrogen peroxide, sodium carbonate or mixtures thereof.

In a seventh embodiment, the present invention is as described above in connection with the preferred embodiment except that: (1) the tracer solution is introduced into the pulp slurry at the entrance of a bleached pulp storage tower and detected at the exit of the tower, (2) the slurry is 4% to 14% solids consistency, and (3) the iodide electrodes are mounted near the stock pump at the exit of the tower.

In an eighth embodiment, the present invention is as described above in connection with the preferred embodiment except that: (1) the tracer solution is introduced into the pulp slurry at the entrance of a machine chest on a paper machine and detected at the exit of a head box of the paper machine, (2) the slurry is 1.5% to 5% solids consistency, and (3) the iodide electrodes are mounted at the exit of the head box.

In a ninth embodiment, the present invention is as described above in connection with the preferred embodiment except that: (1) the tracer solution is introduced into the pulp slurry at the entrance of a machine chest on a pulp machine and detected at the exit of a head box of the pulp machine, (2) the slurry is 1.5% to 5% solids consistency, and (3) the iodide electrodes are mounted at the exit of the head box.

The tracer detection system of the present invention is suitable for measuring pulp retention time in mills with a variety of pulping processes. However, the greatest benefit will be obtained in processes where careful control of chemical stages is most critical, which, in pulp processing, are the bleaching stages. This system will be especially useful in the enzyme treatment stage, which takes place in wide towers which are known to be prone to channeling. The tracer system of the present invention is used preferably with stock flows of 50 to 1500 tonnes per day and the pulp at 1.5% to 30% solids consistency.

The tracer system of the present invention is accurate, compatible with mill operations, and suitable for on-line measurement of pulp residence time distribution. It is therefore uniquely suitable for mill application.

The above specification provides a discussion of the invention and methods of using it. The following Examples illustrate the benefits of the present invention. The Examples are intended to be illustrative only.

8

EXAMPLE 1

Determination of Pulp Retention Time On-Line Measurement of Tracer Concentration With reference to FIG. 1, pulp retention time was measured in enzyme treatment tower 10 of a 900 tonne per day softwood Kraft pulp mill in eastern Canada using an on-line tracer test of the present invention. Tower 10 was 21 meters tall by 15 meters in diameter and was filled to 30% of capacity with pulp. A stock of 12 liters of 25% potassium iodide solution 12 in water was added to a pulp slurry of 10% solids consistency in water. The solution was added by pouring it onto the stock. At the point of tracer addition, the stock was in chute 13 leading to pump 14 that conveys the pulp to the entrance of enzyme treatment tower 10, also called the brownstock storage tower.

At exit 11 of the tower, the pulp slurry is diluted to 3.0% solids consistency with chlorine bleach effluent and then passes through a mixing pump (not shown in FIG. 1) and a pipe 22 on its way to the chlorination tower.

Figure 2:
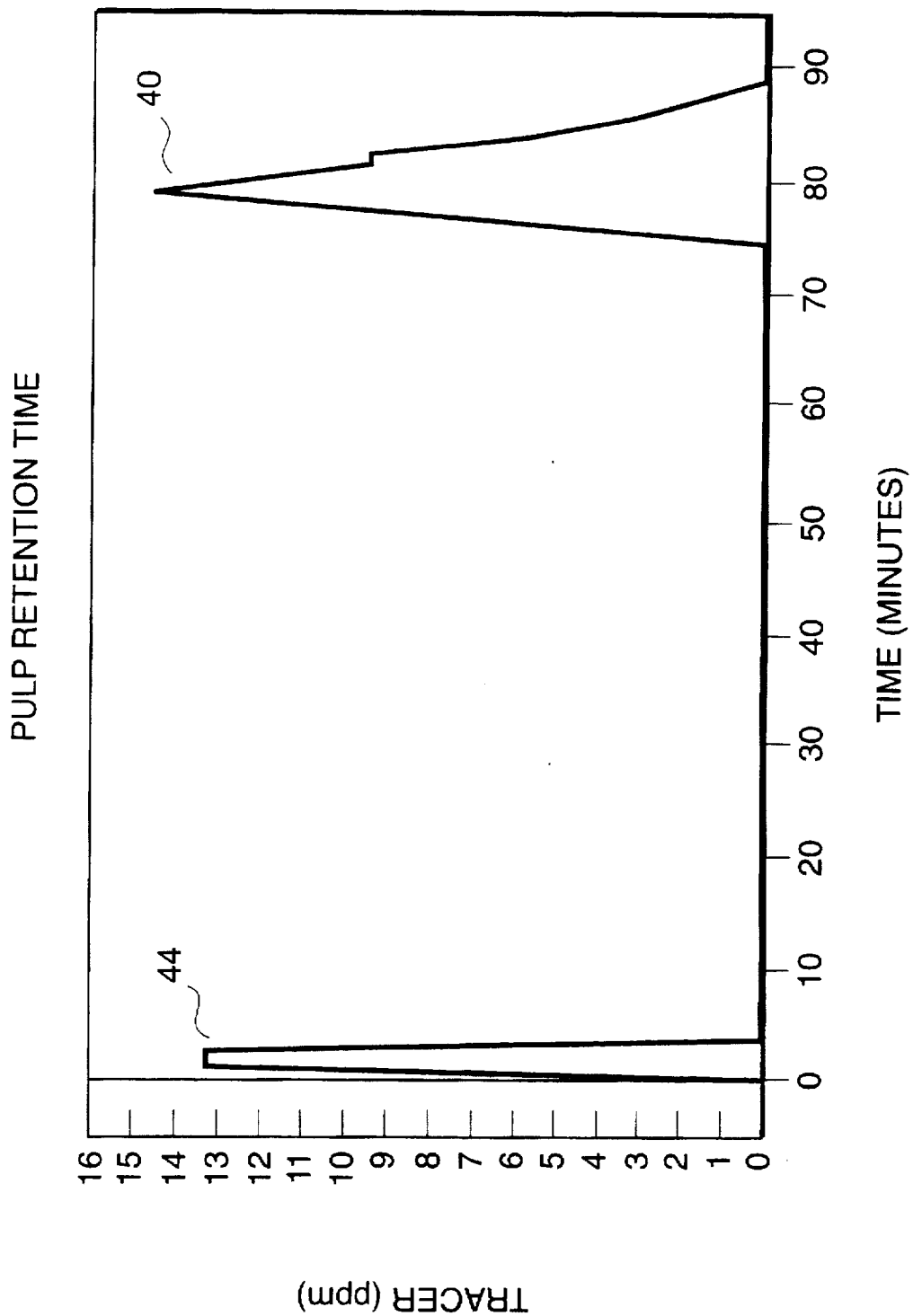
FIG. 2 is a plot of iodide concentration versus time in a pulp slurry.

Orion 94-53 Halide iodide-sensitive probe 18 and reference electrode 20 were mounted on pipe 22 leading to a chlorination tower (not shown in FIG. 1). Starting at the time tracer solution 12 was added to the pulp slurry, the signals for iodide concentration were relayed to Moore 352 controller 24 and then to a computer 26, which calculated and displayed the iodide concentration. The display was a continuous trace of iodide concentration versus time shown in FIG. 2.

The tracer time curve shows two peaks (peaks 44 and 46), indicating that the pulp travels through the tower in two modes. A portion of the pulp goes through immediately, with a residence time of less than 4 minutes. The remaining pulp travels through in 75 to 88 minutes. This "two-peak" retention time is surprising and has not been reported previously.

The continuous measurement allows pulp mill operators to integrate the peaks of tracer concentration and to determine the amount of pulp in each peak. This calculation shows that 25% of the pulp is in the very rapid peak and the remaining 75% is in the slower-moving peak. The inventors speculate that the rapidly moving pulp is traveling in a narrow core down the center of the tower. The remainder of the pulp is probably traveling outside this narrow core. This pulp is flowing at a rate close to that predicted by Bodenheimer.

This residence time distribution identifies a potential problem to the mill which could not have been detected with conventional tracer tests. The 25% of the pulp that resides in the tower for less than 4 minutes will have an inadequate degree of enzyme treatment. After bleaching, this pulp will not be as bright as the pulp that had over one hour residence time. This might cause a nonuniform appearance in the final pulp or a decrease in the benefits obtained from enzyme treatment.

EXAMPLE 2

Determination of Pulp Retention Time/Manual Tracer Test

Concurrently with Example 1, the tracer concentration was monitored manually as described below. Samples were taken manually using standard techniques (every 5 minutes at tower exit 11) and the iodide concentration was measured by a bench-top iodide electrode (not shown in FIG. 1.) The results are listed in Table 1 below.

One peak was observed, corresponding to the tracer breakthrough at 75 minutes after tracer addition. The highest concentration of tracer was detected at 80 minutes, and the last sign of tracer was in the sample taken 85 minutes after tracer addition. The retention time is reported as 80 minutes.

At the 30% level, the tower holds 111 tonnes of pulp at 10% solids consistency. The plug flow retention time is therefore 178 minutes. The measured retention time of 80 minutes is significantly less than this, which indicates that channeling is present in the tower. This is consistent with the teachings of Bodenheimer, who predicts channeling with a 65 minute retention time in a tower with these parameters.

TABLE 1

TRACER CONCENTRATION

| Time (min) | Tracer concentration (ppm) |
|---|---|
| 0 | <1 |
| 5 | <1 |
| 10 | <1 |
| 15 | <1 |
| 20 | <1 |
| 25 | <1 |
| 30 | <1 |
| 35 | <1 |
| 40 | <1 |
| 45 | <1 |
| 50 | <1 |
| 55 | <1 |
| 60 | <1 |
| 65 | <1 |
| 70 | <1 |
| 75 | 3.2 |
| 80 | 9.9 |
| 85 | 4.2 |
| 90 | <1 |
| 95 | <1 |
| 100 | <1 |

The manual measurements of Example 2 agree with the on-line readings of Example 1. However, the conventional 5 minute interval that is generally taught as acceptable between manual readings loses much of the information that was gained in the on-line study. The manual testing does not detect the early peak of less than 4 minutes residence time. Nor does the manual method allow the later peak to be quantified so as to account for all of the pulp in the system. The manual testing reaches the erroneous conclusion that all of the pulp travels through the tower as a plug, and thus does not warn the mill of the potential problem of nonuniform pulp.

EXAMPLE 3

Variation Of Retention Time With Stock Level

A study was undertaken at a pulp mill to determine the retention time when the enzyme treatment tower is 60% full. This study was undertaken to determine whether the pulp retention time is constant at a given pulp level. The pulp retention time was measured at a 1025 tonne per day softwood Kraft pulp mill in western Canada. The tower is 14 meters tall by 10 meters diameter.

A barrel stock of 25% potassium iodide solution in water was made to be poured onto the pulp slurry in 2.0 liter aliquots when desired. The slurry was 6% solids consistency in water. At the point of tracer addition, the stock was at the top of the chute leading to the pump that conveys the pulp to the entrance of the brownstock storage tower.

At the exit of the tower, the pulp was diluted to 4.4% solids consistency with chlorine bleach effluent and then pumped through a mixing pump and through a pipe to the chlorination tower. The tracer concentration was detected on-line as described in Example 1.

The stock level fluctuates from 5% to 100% full over the course of a few days, depending on the pulp production rate and other factors. The stock level was monitored and tracer tests were carried out when the stock level was about 60% full. In all, there were 8 tests conducted over a 34 day period. The results are listed in Table 2 below.

The retention time varied from 18 minutes to 36 minutes. This is surprising, because throughout these tests, all of the variables that are widely thought to influence the retention time were held constant, including tower geometry, pH, temperature, wood species, solids consistency, production rate, and pulp level. Bodenheimer would have predicted a constant retention time under these process conditions. Yet, contrary to conventional wisdom, the retention time varied greatly from day to day strongly suggesting that there must be factors other than those described by Bodenheimer at work.

The convenience of the on-line detection system makes this, and similar, studies possible. With manual sampling and off-line analysis, the burden of testing is too large to carry out tracer tests with this frequency and with short notice. Further, because they lacked the benefits of this invention, previous workers failed to recognize that such differences even needed to be controlled.

TABLE 2

PULP RETENTION TIME WITH TOWER AT 60% OF FULL LEVEL

| Test | Retention time (minutes) |
|---|---|
| 1 | 18 |
| 2 | 28 |
| 3 | 33 |
| 4 | 18 |
| 5 | 36 |
| 6 | 28 |
| 7 | 23 |
| 8 | 31 |

While preferred embodiments of our invention have been shown and described, it is to be understood that the invention is defined solely by the scope of the appended claims.

We claim:

1. A method for determining the residence time of pulp as it moves through a pulp mill comprising the steps of:
    introducing a tracer compound comprising an iodide salt into a pulp slurry at a first location;
    detecting the presence of the tracer compound over a time period by means of an automated detector which senses the presence of free iodide ions at a second location in the pulp mill;
    generating a voltage signal in the automated detector in response to the iodide ions sensed and relaying said signal to a processor by means of a controller; and
    comparing the voltage signal with a calibration curve by means of said processor whereby the amount of said tracer compound is detected in the pulp slurry and related to a pulp residence time, between said first and second locations.

2. The method according to claim 1 wherein the automated detector detects the tracer compound in a pulp slurry that comprises 1.5% to 30% solids, by weight.

3. The method according to claim 1 wherein the automated detector detects the tracer compound in a pulp slurry at a second location proximate to the exit of an enzyme treatment tower of said pulp mill.

4. The method according to claim 3 wherein the tracer compound is introduced into the pulp slurry at a first location which is prior to the pulp slurry being introduced into an enzyme treatment tower.

5. The method according to claim 4 wherein the pulp is washed and then bleached after exiting the enzyme treatment tower.

6. The method according to claim 4 wherein the pulp is bleached after exiting the enzyme treatment tower without first washing the pulp.

7. The method according to claim 1 wherein the automated detector detects the tracer compound in a pulp slurry at a second location proximate to the exit of a digester of said pulp mill.

8. The method according to claim 1 wherein the automated detector detects the tracer compound in a pulp slurry at a second location proximate to the exit of an oxygen delignification reactor or an ozone reactor.

9. The method according to claim 1 wherein the automated detector detects the tracer compound in a pulp slurry at a second location proximate to the exit of a chlorine reactor or an alkali extraction rector.

10. The method according to claim 1 wherein the automated detector detects the tracer compound in a pulp slurry at a second location proximate to the exit of a bleached pulp storage tower, or at the head box of a pulp machine or paper machine.

* * * * *